US010564316B2

(12) United States Patent
Xu et al.

(10) Patent No.: US 10,564,316 B2
(45) Date of Patent: Feb. 18, 2020

(54) FORECASTING NATIONAL CROP YIELD DURING THE GROWING SEASON

(71) Applicant: The Climate Corporation, San Francisco, CA (US)

(72) Inventors: Ying Xu, Berkeley, CA (US); Lijuan Xu, Foster City, CA (US)

(73) Assignee: The Climate Corporation, San Francisco, CA (US)

( * ) Notice: Subject to any disclaimer, the term of this patent is extended or adjusted under 35 U.S.C. 154(b) by 241 days.

(21) Appl. No.: 14/675,992

(22) Filed: Apr. 1, 2015

(65) Prior Publication Data

US 2016/0290918 A1    Oct. 6, 2016

(51) Int. Cl.
*G01V 99/00*    (2009.01)
*G01N 21/359*    (2014.01)
(Continued)

(52) U.S. Cl.
CPC ......... *G01V 99/005* (2013.01); *G01N 21/359* (2013.01); *G01N 33/0098* (2013.01);
(Continued)

(58) Field of Classification Search
CPC ......... A01B 79/005; G01N 2021/1793; G01N 2021/3155; G01N 21/359;
(Continued)

(56) References Cited

U.S. PATENT DOCUMENTS

| 5,796,932 A | 8/1998 | Fox |
| 9,087,312 B1 * | 7/2015 | Mewes ................. G06Q 50/02 |

(Continued)

FOREIGN PATENT DOCUMENTS

| WO | WO 2009/048341 A1 | 4/2009 |
| WO | WO 2011/064445 A1 | 6/2011 |
| WO | WO 2014/036281 A2 | 3/2014 |

OTHER PUBLICATIONS

European Patent Office, "Search Report" in application No. PCT/US2016/023348, dated May 30, 2016, 13 pages.

(Continued)

*Primary Examiner* — Mohammed Shamsuzzaman
(74) *Attorney, Agent, or Firm* — Hickman Palermo Becker Bingham LLP; Sanjeev S. Bajwa

(57) ABSTRACT

A method for determining national crop yields during the growing season using regional agricultural data is provided. In an embodiment, determining national crop yields during the growing season may be accomplished using a server computer system that receives, via a network, agricultural data records that are used to forecast a national crop yield for a particular year. Within the server computer system an agricultural time series module receives one or more agricultural data records that represent a type of covariate data value related to plants at a specific geo-location at a specific time. The agricultural time series module then aggregates the agricultural data records to create one or more geo-specific time series that represent a specific geo-location over a specified time. The agricultural time series module creates one or more aggregated time series that represent geographic areas from a subset of the one or more geo-specific time series. A crop yield estimating module selects a representative feature from the one or more aggregated time series and creates a covariate matrix for each specific geographic area in computer memory of the server computer system. The crop yield estimating module determines a specific state crop yield for a specific year by using a linear regression module to calculate the specific state crop yield from the covariate matrix that represents the specific state for that specific year. The crop estimation module determines a national crop yield for the specific year by using the distribution generation module to calculate the national crop yield for a specific year from the sum of the specific state crop yields for the specific year nationally adjusted using a national yield adjustment module.

18 Claims, 5 Drawing Sheets

(51) Int. Cl.
  *G01N 33/00* (2006.01)
  *G06Q 10/04* (2012.01)
  *G01W 1/10* (2006.01)
  *G01N 33/24* (2006.01)
  *G01N 21/17* (2006.01)
  *G01N 21/31* (2006.01)
  *A01B 79/00* (2006.01)

(52) U.S. Cl.
  CPC .............. *G01N 33/24* (2013.01); *G01W 1/10* (2013.01); *G06Q 10/04* (2013.01); *A01B 79/005* (2013.01); *G01N 2021/1793* (2013.01); *G01N 2021/3155* (2013.01); *G01N 2201/0616* (2013.01); *G01N 2201/129* (2013.01)

(58) Field of Classification Search
  CPC ..... G01N 2201/0616; G01N 2201/129; G01N 33/0098; G01W 1/10; G06Q 10/04
  USPC .............. 702/179, 19; 705/37, 35, 4; 703/11
  See application file for complete search history.

(56) References Cited

U.S. PATENT DOCUMENTS

| | | | |
|---|---|---|---|
| 2002/0133505 | A1 | 9/2002 | Kuji |
| 2002/0183867 | A1 | 12/2002 | Gupta |
| 2003/0061075 | A1* | 3/2003 | Heckman ............... G06Q 40/08 705/4 |
| 2005/0027572 | A1* | 2/2005 | Goshert ................. G06Q 40/02 705/4 |
| 2005/0234691 | A1* | 10/2005 | Singh ..................... G06Q 10/04 703/11 |
| 2006/0004907 | A1 | 1/2006 | Pape |
| 2006/0167926 | A1 | 7/2006 | Verhey et al. |
| 2007/0085673 | A1 | 4/2007 | Krumm |
| 2007/0174095 | A1* | 7/2007 | McComb ........... G06Q 10/0635 705/4 |
| 2008/0287662 | A1 | 11/2008 | Wiesman |
| 2013/0173321 | A1 | 7/2013 | Johnson |
| 2013/0174040 | A1 | 7/2013 | Johnson |
| 2013/0332205 | A1 | 12/2013 | Friedberg |
| 2014/0012732 | A1* | 1/2014 | Lindores .............. A01B 79/005 705/37 |
| 2014/0089045 | A1 | 3/2014 | Johnson |
| 2014/0321714 | A1* | 10/2014 | Masten .............. G06K 9/00657 382/110 |
| 2015/0026023 | A1* | 1/2015 | Sirota .................... G06Q 50/02 705/35 |
| 2015/0370935 | A1 | 12/2015 | Starr |
| 2016/0078375 | A1 | 3/2016 | Ethington et al. |
| 2016/0078569 | A1 | 3/2016 | Ethington et al. |
| 2016/0078570 | A1 | 3/2016 | Ethington et al. |
| 2016/0171680 | A1* | 6/2016 | Lobell ................. G06K 9/6212 382/110 |
| 2017/0213141 | A1* | 7/2017 | Xu ......................... G06N 7/005 |

OTHER PUBLICATIONS

European Claims in application No. PCT/US2016/023348, dated May 2016, 6 pages.
European Patent Office, "Search Report", in application No. PCT/US2015/049456, dated Nov. 9, 2015, 13 pages.
European Patent Office, "Search Report" in application No. PCT/US2015/049466 dated Nov. 9, 2015, 12 pages.
European Patent Office, "Search Report" in application No. PCT/US2015/049464, dated Nov. 9, 2015, 11 pages.
European Claims in application No. PCT/US2015/049466, dated Nov. 2015, 5 pages.
European Claims in application No. PCT/US2015/049464, dated Nov. 2015, 7 pages.
European Claims in application No. PCT/2015/049456 dated Nov. 2015, 7 pages.
International Bureau of WIPO, "Search Report" in application No. PCT/US2016/023348, dated Oct. 3, 2017, 9 pages.
Current Claims in application No. PCT/US2016/023348, dated Oct. 2017, 6 pages.
Ethingon, U.S. Appl. No. 14/846,422, filed Sep. 4, 2015, Office Action, dated Feb. 2, 2018.
European Patent Office, "Search Report" in application No. 15 775 530.7-1217, dated Sep. 13, 2018, 6 pages.
European Claims in application No. 15 775 530.7-1217, dated Sep. 2018, 4 pages.
Ethington, U.S. Appl. No. 14/846,659, filed Sep. 4, 2015, Interview Sumary, dated Aug. 3, 2018.
Ethington, U.S. Appl. No. 14/846,422, filed Sep. 4, 2015, Final Office Action, dated Aug. 29, 2018.
Ethington, U.S. Appl. No. 14/846,661, filed Sep. 4, 2015, Office Action, dated May 17, 2018.
Ethington, U.S. Appl. No. 14/846,659, filed Sep. 4, 2015, Office Action, dated Apr. 30, 2018.
Ethington, U.S. Appl. No. 14/846,454, filed Sep. 4, 2015, Office Action, dated May 17, 2018.
Ethington, U.S. Appl. No. 14/846,661, filed Sep. 4, 2015, Interview Summary, dated Feb. 20, 2019.
Ethington, U.S. Appl. No. 14/846,454, filed Sep. 4, 2015, Final Office Action, dated Jan. 2, 2019.
Ethington, U.S. Appl. No. 14/846,422, filed Sep. 4, 2015, Office Action, dated Jan. 30, 2019.
Ethington, U.S. Appl. No. 14/846,659, filed Sep. 4, 2015, Final Office Action, dated Oct. 5, 2018.
Ethington, U.S. Appl. No. 14/846,454, filed Sep. 4, 2015, Office Action, dated Jun. 27, 2019.
Ethington, U.S. Appl. No. 14/846,661, filed 096/04/2015, Office Action, dated Jun. 27, 2019.
Ethington, U.S. Appl. No. 14/846,422, filed Sep. 4, 2015, Interview Summary, dated Mar. 7, 2019.

* cited by examiner

FORECASTING NATIONAL CROP YIELD DURING THE GROWING SEASON

CROSS-REFERENCE TO RELATED APPLICATIONS

This application is related to Provisional Application 62/049,898, filed Sep. 12, 2014, entitled "Method and Systems for Managing Agricultural Activities", the entire disclosure of which is hereby incorporated by reference as if fully set forth herein.

This application is related to Provisional Application 62/049,937, filed Sep. 12, 2014, entitled "Method and Systems for Recommending Agricultural Activities", the entire disclosure of which is hereby incorporated by reference as if fully set forth herein.

This application is related to Provisional Application 62/049,909, filed Sep. 12, 2014, entitled "Method and Systems for Determining Agricultural Revenue", the entire disclosure of which is hereby incorporated by reference as if fully set forth herein.

This application is related to Provisional Application 62/049,929, filed Sep. 12, 2014, entitled "Method and Systems for Managing Crop Harvesting Activities", the entire disclosure of which is hereby incorporated by reference as if fully set forth herein.

FIELD OF THE DISCLOSURE

The present disclosure relates to computer systems and computer-implemented methods that are configured for creating data values that are useful in forecasting an agricultural crop yield for an entire country, during a growing season, based on regional data measurements over a specific time period.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section Agricultural production requires significant strategy and analysis. In many cases, agricultural growers, such as farmers or others involved in agricultural cultivation, are required to analyze a variety of data to make strategic decisions before and during the crop cultivation period. In making such strategic decisions, growers rely on computer-implemented crop yield forecast models to determine their cultivation strategy. Crop yield forecast models may help a grower decide how to spend or conserve in key areas that affect cultivation, such as fuel and resource costs, equipment investments, crop related insurance, and crop cultivation manpower.

Crop yield forecast models also are commonly used by insurance companies and risk management companies to calculate premiums based upon certain risk factors. For example, crop revenue insurance is an insurance policy that protects a farmer's projected crop revenue for a given year and covers a decline in price that occurs during the crop growing season. Such crop revenue coverage is based on determining a deviation from the mean projected revenue of the crop. For insurance companies to create profitable crop revenue insurance plans, the insurance companies must have accurate crop yield forecast models to accurately estimate the revenue of a farmer.

However, most measurements of crop production occur at the end of a growing season, and are prepared on a local or regional basis. In a large country such as the United States, obtaining accurate crop yield forecasts at the national level, and during the growing season, has been a challenge for farmers and insurance companies. Local and regional measurements are numerous and prepared in widely geographically distributed areas, and are difficult to obtain when farmers are in the growing season and occupied by other critical growing tasks. Consequently, one of the challenges in creating an accurate crop yield forecast model is simply obtaining data useful to create a national crop yield forecast model during the growing season. One approach has been to use data provided by the United States Department of Agriculture's National Agricultural Statistics Service (NASS). NASS conducts a survey-based data collection technique, where it conducts an agricultural yield survey multiple times during a year. The survey is provided directly to farmers across the country and asks the farmers to report their crop conditions at that time of year. However, this approach is not particularly useful for forecasting during the growing season because farmers are unable to provide a good estimate of their crop yield until harvest time approaches, at the end of the growing season.

Other approaches for predicting accurate crop yields during the growing season may involve using crop simulation process models, for example, to predict regional corn yields. The drawbacks to this approach are that process models require a multitude of local inputs including weather and climate conditions, soil conditions, and data points covering a large set of farming regions. These inputs then need to be calibrated in order to be accurate. The cost for collecting a high number of local inputs and calibrating the parameters make process modelling too expensive to feasibly use at a national level.

Methods for analyzing a limited number of crop related data during the growing season and modelling crop yields at a national level are desirable.

DETAILED DESCRIPTION

Figure 1:
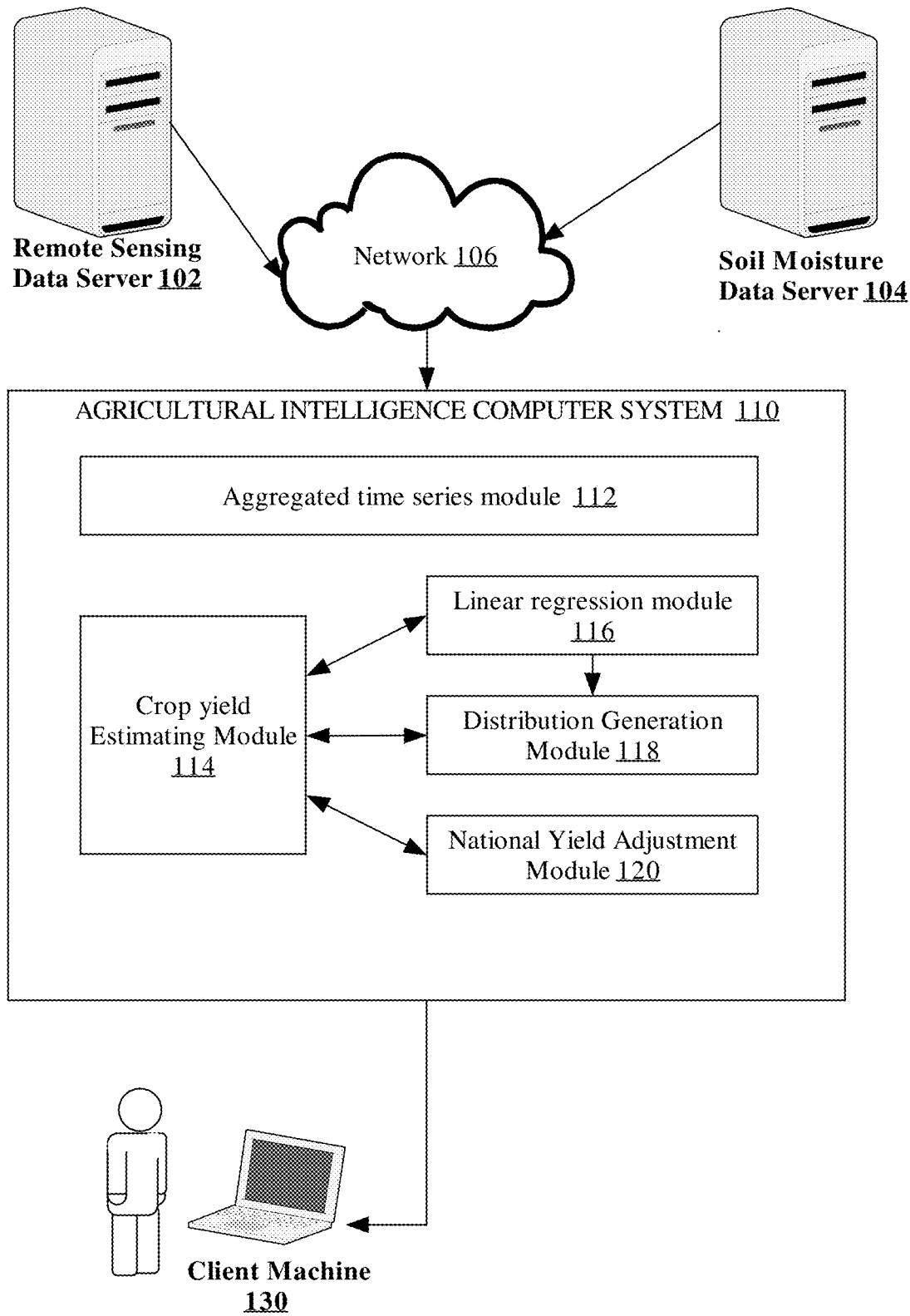
FIG. 1 illustrates an embodiment of an agricultural intelligence computer system.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

General Overview

A computer system and computer-implemented method that are configured for determining national crop yields during the growing season using regional agricultural data is provided. In an embodiment, determining national crop yields during the growing season may be accomplished using a server computer system that receives, via a network, agricultural data records that are used to forecast a national crop yield for a particular year. Within the server computer system an agricultural time series module receives one or more agricultural data records that represent a type of covariate data value related to plants at a specific geo-location at a specific time. The types of covariate data values may include remotely sensed spectral property records of plants within a particular spectral bandwidth range and soil moisture data records. Remote sensing uses electronic digital sensing equipment that may be aerial, satellite-based or local, as further described. The agricultural time series module then aggregates the agricultural data records to create one or more geo-specific time series that represent a specific geo-location over a specified time. The agricultural time series module creates one or more aggregated time series that represent geographic areas from a subset of the one or more geo-specific time series.

A crop yield estimating module then selects a representative feature from the one or more aggregated time series and creates a covariate matrix for each specific geographic area in computer memory of the server computer system. The covariate matrix contains the representative features selected from the one or more aggregate time series. In the case of a nation that is organized as a federation of states, the crop yield estimating module then determines a specific state crop yield for a specific year by using a linear regression module to calculate the specific state crop yield from the covariate matrix that represents the specific state for that specific year. The parameters of the linear regression module include regression coefficients that are calculated using a distribution generation module and an error term that is calculated using the distribution generation module where the mean parameter for the error term is zero and the variance parameter is a state specific bias coefficient.

After determining state specific crop yields, the crop estimation module determines a national crop yield for the specific year by using the distribution generation module to calculate the national crop yield for a specific year from the sum of the specific state crop yields for the specific year nationally adjusted using a national yield adjustment module. In an embodiment, the crop yield may refer to a specific crop yield such as corn yield.

Structural Overview

In an embodiment, an agricultural intelligence computer system, comprising one or more computer programs or other software elements, or computer-implemented logic is configured to determine a national crop yield during the growing season from agricultural data values from one or more sources. The agricultural intelligence computer system is connected, via a network, to one or more agricultural data resources. The agricultural intelligence computer system utilizes the agricultural data resources to query different covariate data points, which are then used to calculate a national crop yield for a specific year. Covariate data refers to independent variables that may be used in forecasting crop yields. In this context, the covariate data refers to different agricultural data records that are related to crop cultivation areas such as plant density and maturity information for specific crops on farmland or soil information related to the composition of the farmland soil and the water saturation level of the farmland soil. Specifically, agricultural data records may include, but are not limited to, regional agricultural data related to remotely sensed signals and soil moisture data.

Remote sensing refers to the use of sensor technologies used to detect and classify objects on Earth by means of propagated signals. In an embodiment, remotely sensed signals are detected using Moderate Resolution Imaging Spectroradiometer (MODIS). MODIS is aboard the NASA satellites Terra and Aqua at the time of this writing, and provides a scan of the earth using 36 spectral bands, or groups of wavelengths. The level of resolution for each pixel may be measured down to a specified granularity in meters. Different spectral bands may be measured using different meter resolutions which include, but are not limited to, 250 meters, 500 meters, and 1000 meters. Different remotely sensed signals may be used to detect levels of vegetation on earth, as further described in the REMOTE SENSING section herein.

Soil moisture data may be used to determine the level of saturation of land and whether or not particular areas of farmland have soil moisture levels that indicate drought regions. In an embodiment, soil moisture data may be obtained from NASA's Land Data Assimilation Systems (LDAS) servers. LDAS is a project designed to collect and construct land surface model datasets from precipitation data, to record the soil moisture across various regions. In an embodiment, soil moisture datasets may be obtained by digital query messages from an application computer to LDAS server computers in which the queries request soil moisture data for particular regions of interest, as discussed in the SOIL MOISTURE DATA section herein.

FIG. 1 depicts an embodiment of an example agricultural intelligence computer system connected to one or more agricultural data resources and a client device. In an embodiment, the agricultural intelligence computer system 110 is connected via a network 106 to an external remote sensing data server 102, a soil moisture data server 104 and a client machine 130. For purposes of illustrating a clear example, FIG. 1 shows single instances of the foregoing elements, but practical embodiments may include clusters of computers in any number, and one or more of the elements may be implemented using multiple physical or virtual server instances in data centers, cloud computer centers, and the like.

The remote sensing data server 102 comprises a data repository that stores remotely sensed signals for specific land areas at a specific time. The agricultural intelligence computer system 110 may retrieve remotely sensed data related to a specific geo-location and time on-demand and process the remotely sensed data to produce a crop yield forecast. Alternatively, the agricultural intelligence computer system 110 may include one or more data storage servers used to store remotely sensed data queried from the remote sensing data server 102 for future data processing.

In an embodiment, the soil moisture data server 104 contains soil moisture datasets of measured precipitation data for a specific geo-location at a specific time. The agricultural intelligence computer system 110 may retrieve soil moisture data for the purposes of computing a crop yield forecast or for storing the soil moisture data in one or more internal data storage servers within the agricultural intelligence computer system 110.

In an embodiment, the agricultural intelligence computer system 110 comprises a plurality of interconnected logic modules that are configured to transform the raw agricultural data from the remote sensing data server 102 and the soil moisture data server 104 into a crop yield forecast model. As seen in FIG. 1, in one embodiment, agricultural intelligence computer system 110 comprises an aggregated time series module coupled to a crop yield estimating module 114, linear regression module 116, distribution generation module 118, and national yield adjustment module 120. Each of the modules may be implemented in various embodiments using one or more computer programs, other software elements, firmware, hardware logic such as FPGAs or ASICs, or any combination of the foregoing.

The aggregated time series module 112 is configured to receive the agricultural data retrieved from the data servers and aggregate the individual data records into a time series. "Time series," in this disclosure, refers to digital data that may be electronically stored in main memory or in digital electronic storage devices associated with the agricultural intelligence computer system 110. A time series is a collection of data values that represent a specific area over multiple time periods. For example, an aggregated times series may contain remotely sensed data values for a specific geo-location where each data value represents an 8-day period and the entire time series spans the course of one year. Time series data is especially useful when developing forecast models. For example, the aggregated time series of remotely sensed data values over a partial period of a year may be used to forecast the crop yield distribution in upcoming months of that year, which in turn could be used to forecast the crop yield for that given year. The aggregated time series module 112 then further aggregates the time series data into larger sets of time series that represent a geographic area such as an entire state.

The aggregated time series module 112 is configured, after aggregating the agricultural data values, to send the aggregated time series to the crop yield estimating module 114. The crop yield estimating module 114 is configured to receive multiple time series, each representing a measured covariate for a specific region. The crop yield estimating module 114 selects a representative feature from each of the multiple time series. In an embodiment, the maximum value of the time series is selected to represent a particular covariate time series for the geographic area.

The crop yield estimating module 114 is configured to perform, after selecting a representative feature for each covariate time series, creating a covariate matrix for each defined geographic area made up of the selected representative values. Each covariate matrix that is created using this approach comprises a set of digital data that is electronically stored in a digital electronic mass storage device that is coupled to the agricultural intelligence computer system 110, or in main memory of the agricultural intelligence computer system 110. In an embodiment a defined geographic area may be each of the crop producing states. Therefore each covariate matrix can represent each corn producing state and contain the representative covariate time series values for that state.

The crop yield estimating module 114 is configured to determine a state specific crop yield by communicating with a linear regression module 116. The linear regression module 116 is configured or programmed to determine the state specific crop yield using a linear regression function on the state specific covariate matrix, resulting in creating and storing digital data in memory or in a mass storage data representing output of the linear regression function. To determine the state specific crop yield for that particular year, the linear regression module 116 is programmed to use a specified state specific $\beta$ regression coefficient and $\varepsilon$ error term. In order to determine the $\beta$ regression coefficient and $\varepsilon$ error term for a particular state, the linear regression module 116 communicates with the distribution generation module 118.

The distribution generation module 118 is configured or programmed to determine state specific distribution values and to store the values as digital data in memory or a mass storage device of the agricultural intelligence computer system 110. In an embodiment, the distribution calculated is a normal distribution for a state specific $\beta$ coefficient and $\varepsilon$ error value are determined using an independently and identically distributed random variable from a normal distribution function and historical data from previously measured years. Once the distribution generation module 118 determines the $\beta$ regression coefficient and $\varepsilon$ error term for a particular state, it returns the values to the linear regression module 116. The linear regression module 116 is programmed to use the covariate matrix, the $\beta$ regression coefficient and $\varepsilon$ error term to determine a yield value for the specific state as digital data, and to communicate the yield value to the crop yield estimating module 114.

The crop yield estimating module 114 is programmed, in response to receiving the state specific yield value, for all states requested, to determine the national yield for a specific year by communicating with the national yield adjustment module 120 and the distribution generation module 118.

In an embodiment, the national yield adjustment module 120 is programmed to calculate bias and error coefficients that may be associated with incomplete sampling of state yields, and to store bias and error coefficients as digital data in memory or a mass storage device of the agricultural intelligence computer system 110. For instance, if one or more states sampled contained incomplete data, then their forecasted state yield may skew the national forecasted yield, and the national yield adjustment module 120 may be programmed to determine bias and error coefficients to offset or compensate for such skew.

The crop yield estimating module 114 is programmed, after receiving bias and error coefficients from the national yield adjustment module 120, to request an independent and identically distributed random variable from the distribution generation module 118 using the sum of the state specific yields and the received bias and error coefficients.

In response to computing the national crop yield for a specified year, the agricultural intelligence computer system 110 is programmed to receive the national crop yield from the crop yield estimating module 114. The national crop yield may include a single predicted value, a level of uncertainty associated to that predicted value, and the whole probability distribution associated to that predicted value. In an embodiment, the agricultural intelligence computer system 110 may be programmed to send the national yield information to a client machine 130. For example, the client machine 130 may host or execute an application program or app that is compatible with the agricultural intelligence computer system 110 and that is programmed to receive or poll for the national yield information and display the national yield information in response to a user query, or an app function, using a graphical user interface or other output means programmed in the client machine. In another embodiment, the agricultural intelligence computer system 110 may be programmed to store the national yield information for the purpose to refining future national forecasts.

An embodiment of the client machine 130 may include, but is not limited to, a desktop computer or laptop computer running a crop yield forecasting client program for use by a farmer or an insurance company. Other embodiments of the client machine 130 may include portable computing devices such as a tablet computer or smartphone.

Functional Overview

Figure 2:
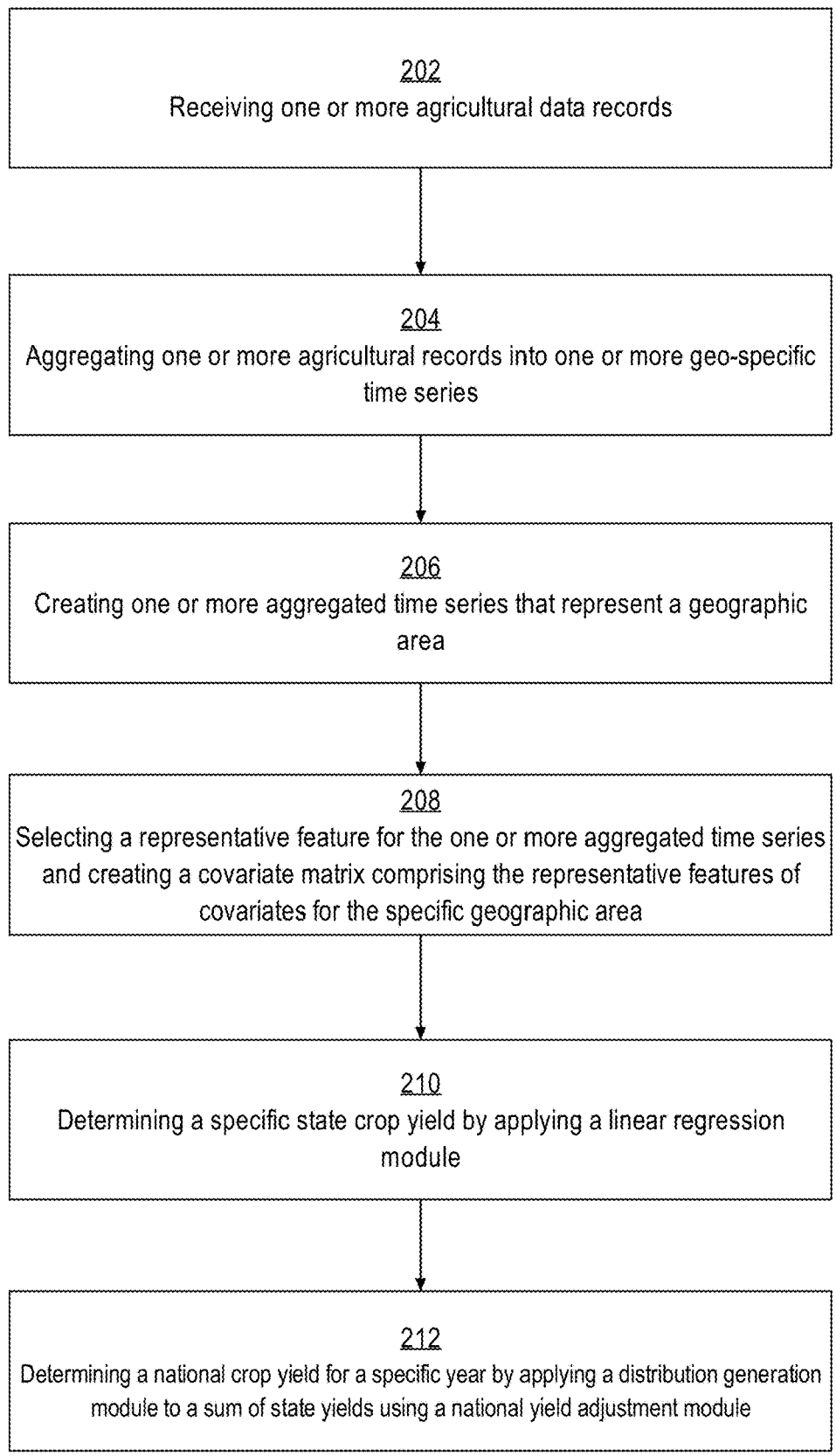
FIG. 2 illustrates a computer-implemented process for receiving agricultural data records, aggregating the agricultural data records to create a time series for a geographic area, and determining state and national crop yields.

FIG. 2 is a flow diagram that depicts a process for determining a national crop yield for a specified year using covariate data points measured at a more granular level. FIG. 2 may be implemented, in one embodiment, by programming the elements of agricultural intelligence computer system 110 to perform the functions that are described in this section, which may represent disclosure of an algorithm for computer implementation of the functions that are described. For purposes of illustrating a clear example, FIG. 2 is described in connection with certain elements of FIG. 1. However, other embodiments of FIG. 2 may be practiced in many other contexts and references herein to units of FIG. 1 are merely examples that are not intended to limit the broader scope of FIG. 2.

At block 202, one or more agricultural data records are received. For example, the aggregated time series module 112 receives one or more agricultural data records. The agricultural data records may include remotely sensed signals or soil moisture data samples for a specific geo-location and specific time period. The purpose of receiving the agricultural data records is to compile time series collections that represent data over a specific period of time for a specific geo-location.

At block 204, the agricultural data records are aggregated for specific geo-locations into multiple geo-specific time series. For example, the aggregated time series module 112 aggregates the agricultural data records for specific geo-locations into multiple geo-specific time series. For example, if remotely sensed signal data received covers several time periods from January to August for specific geo-locations in Iowa then the aggregated time series module 112 would aggregate for each geo-location in Iowa, a time series that includes data points from January up until August.

The aggregated time series module 112 aggregates the agricultural data records for specific geo-locations into multiple geo-specific time series. In an embodiment, the aggregated time series module 112 may filter out agricultural data values that correspond to non-agricultural regions. In an embodiment, agricultural regions may be identified from non-agricultural regions using a Common Land Unit data repository. A Common Land Unit (CLU) refers to the smallest unit of land that has a permanent, contiguous boundary. CLUs are used by the farming industry to delineate between identified farmland and other types of land. Other embodiments may use different data repositories to distinguish agricultural regions from non-agricultural regions. By filtering out non-agricultural regions, the aggregated time series module 112 can ensure more accurate sets of geo-specific time series.

At block 206, the process creates one or more aggregated time series that each represents a specific geographic area. For example, the aggregated time series module 112 creates one or more aggregated time series that each represents a specific geographic area. For instance, a geographic area may be defined as a crop producing state such as Iowa. In this case, the aggregated time series module 112 would take every time series representing a geo-location within the boundary of Iowa and aggregate them to create a single time series to represent Iowa's remotely sensed signals. In an embodiment, before aggregating the multiple time series into a single time series, each time series may be preprocessed, using techniques such as locally weighted scatterplot smoothing, to remove erratic data points. By removing erratic data points the step of aggregating the multiple time series into a single series results in a more accurate representation of the multiple time series. In an embodiment, the median of the multiple time series within Iowa would be used as the time series value for each measured day of the year. By using the median value of each time series, the aggregated time series has an approximate representation of the crop yield over the entire state. Other embodiments of determining the aggregated time series for a geographic location are discussed in the AGGREGATED TIME SERIES section herein.

Figure 3:
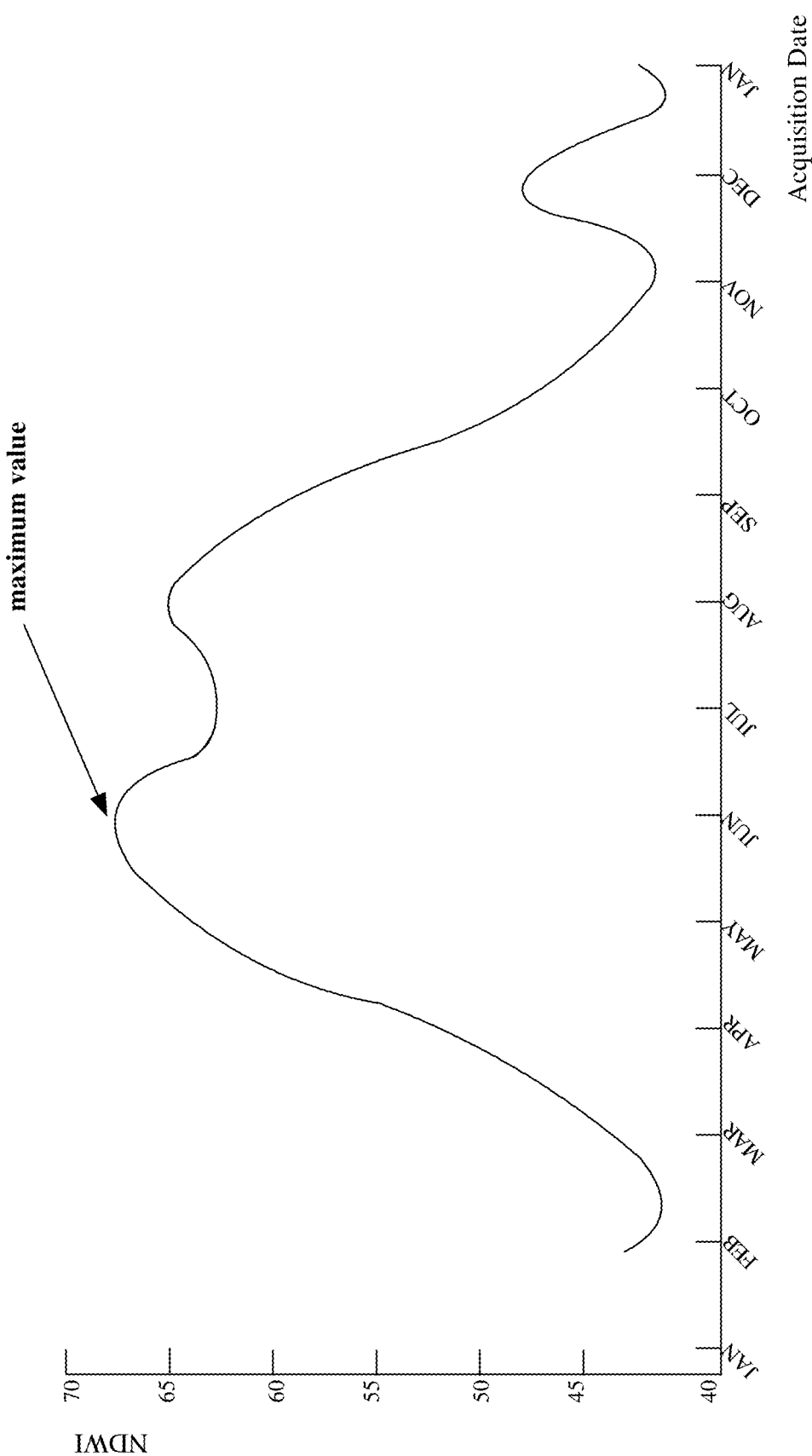
FIG. 3 illustrates an aggregated time series graph for a specific geographic area.

At block 208, the process selects representative features for the one or more aggregated time series. For example, the crop yield estimating module 114 selects a representative feature for the one or more aggregated time series. The purpose of a representative feature for each aggregated time series is to temporally align the multiple data points for each day period to the yearly crop yield output; therefore selecting representative features of the aggregated time series is needed to properly forecast a yearly output. In an embodiment, the maximum value of the time series is selected to represent aggregated time series. For example, FIG. 3 depicts an aggregated time series for Iowa. The maximum value measured at 67.6 NDWI on Jun. 15, 2014. Therefore the crop yield estimating module 114 would select 67.6 NDWI as the representative feature for the NDWI covariate for Iowa. Other embodiments of time series feature selections are discussed in the TIME SERIES FEATURES sections herein.

After selecting a representative feature in each aggregated time series, in an embodiment, the crop yield estimating module 114 creates a covariate matrix which includes the values of each representative feature from each covariate for a specific geographic area. For instance, the covariate matrix for the geographic area that represents the state of Iowa will consist of maximum values for each covariate received from the remote sensing data server 102 and the soil moisture data server 104.

At block 210, a state specific crop yield is determined. For example, the crop yield estimating module 114 determines a state specific crop yield by requesting the linear regression module 116 to determine a predicted state crop yield using the created covariate matrix for that specific state. The linear regression module 116 determines a predicted state crop yield by creating a linear regression model. Linear regression is an approach for modeling the relationship between a dependent variable and independent variables. In this context, the dependent variable is the state crop yield, and the one or more independent variables are the covariate values in the covariate matrix. The linear regression model assumes that the relationship between the dependent variable and the one or more independent variables is linear. This relationship is modeled through an error term $\varepsilon_i$, which is an unobserved random variable. Statistical estimation is incorporated using a regression coefficient, $\beta_s$.

In one embodiment, linear regression module 116 is programmed to determine the state crop yield for a specific year using logic that implements the following function:

$$Y_{s,t} = X^T_{s,t}(\beta_s) + \varepsilon_{s,t}$$

Where:

$Y_{s,t}$: equals the state yield for state S for a given year T.

$X_{s,t}$: equals the covariate matrix of state S in year T up to an observational date.

$\beta_s$: equals the regression coefficient for state S.

$\varepsilon_{s,t}$: equals the error term for state S in year T.

In order for the linear regression module 116 to determine the state crop yield, it first determines the β regression coefficient and ε error term.

For example, the distribution generation module 118 may be programmed to determine the β regression coefficient and ε error term for a given state for a given year. The linear regression module 116 requests distribution generation module 118 to return the β regression coefficient and ε error term for the given state and year. In an embodiment, the distribution generation module 118 may use historical data to determine the β regression coefficient and ε error term. The distribution generation module 118 is programmed to determine the β regression coefficient and ε error term by using an independently and identically distributed random variable from a normal distribution function as illustrated below.

$$\beta_s \sim^{iis} N(\beta_0, \Sigma_0)$$

$$\varepsilon_{s,t} \sim^{iis} N(0, \sigma_s^2)$$

A normal distribution is a function that represents the distribution of many random variables as a symmetrical bell-shaped graph. It is denoted by the function $N(\mu, \sigma)$, where $\mu$ represents the mean or expectation of the distribution and $\sigma^2$ represents the variance. In this case the normal distribution functions are independently and identically distributed random variables, so that each random variable has the same probability distribution as the others and all random variables are mutually independent.

After the distribution generation module 118 determines the β regression coefficient and ε error term the distribution generation module 118 returns the values to the linear regression module 116. The linear regression module 116 then determines a predicted state yield for the particular state and year provided by the crop yield estimating module 114. The determined state yield is the expected value for the state crop yield. In an embodiment, the linear regression module 116 determines the expected value of the state crop yield by recalculating the state crop yield using the linear regression model a configured number of times to determine the mean state crop yield. The linear regression module 116 then returns the expected state crop yield value to the crop yield estimating module 114. The crop yield estimating module 114 repeats this process to determine the state yields for all states that have a covariate matrix.

In another embodiment, the crop yield estimating module 114 may have covariate matrices based upon a different geographical area such as county-wide regions. In this case the crop yield estimating module 114 would request crop yield projections at a county level from the linear regression module 116. In yet other embodiments, the size and shape of the geographic area may be configurable.

At block 212, a national yield is created for the specific year using the previously determined state crop yields and accounting for particular national adjustment factors. For example, the crop yield estimating module 114 determines the national yield for the specific year using the previously determined state crop yields accounting for particular national adjustment factors. The crop yield estimating module 114 first sends the set of state crop yields to the national yield adjustment module 120.

The national yield adjustment module 120 determines how much weight each state should be given relative to one another. For example, if Iowa produces on average twice as much crop than Nebraska, then Iowa's weighted factor would be twice as large as Nebraska's weighted factor. Since each state crop yield received by the national yield adjustment module 120 is a prediction, the national yield adjustment module 120 uses three bias coefficients, $\alpha$, $\gamma$, $\sigma^2$, to account for biases and errors caused by incomplete sampling of state yields. The national yield adjustment module 120 then returns the state weights and bias coefficients to the crop yield estimating module 114. The crop yield estimating module 114 then requests a normal distribution from the distribution generation module 118 where the mean and variance are the sum of the state crop yields accounting for the bias coefficients. The normal distribution function for the national yield is as follows:

$$Y_t \sim^{iiid} N(\alpha + \gamma \tau_s w_{t,s} \mu_{t,s}, \gamma^2 \Sigma_s w_{L,s}^2 \sigma_s^2 + \sigma^2)$$

The notation is as follows:

$\mu_{t,s}$: equals the expected value of $Y_{t,s}$.

$w_{t,s}$: equals the weighted value given to each state relative to the other states for that given year.

$\sigma_s^2$: equals the variance for that specific state.

$\Sigma_s w_{t,s} \mu_{t,s}$: equals the sum of the state crop yield expected values multiplied by their respective weights.

$\alpha$, $\gamma$, $\sigma^2$: are first, second, and third national bias coefficients.

$\Sigma_s w_{t,s}^2 \sigma_s^2$: equals the sum of the state specific variance multiplied by their respective weights squared.

After calculating the predicted national crop yield, using the distribution generation module 118, the crop yield estimating module 114 creates a crop yield estimate for the particular year requested.

In an embodiment, the national crop yield estimate may include a set of values including, but not limited to, a national crop yield value, a prediction interval for the national crop yield value, and a distribution set associated with the predicted national crop yield value.

The prediction interval associated with the national crop yield is a range calculated by the crop yield estimation module 114, which is expected to cover the true national yield value with certain probability. When the probability of covering the true national yield is fixed, the narrower the prediction intervals the more certain the national yield prediction is. For example, crop yield estimating module 114 may be configured to calculate a prediction interval that is expected to cover the true national crop yield 90% of the time. In this example, if the predicted national crop yield is 165 bushels per acre and the prediction interval range is a very small range, such as 155-170 bushels per acre, then the certainty associated with the predicted national crop yield is very high because over 90% of the predictions resulted in a very narrow range of values. However, if in the previous example the prediction interval is 120-200 bushels per acre, then the certainty associated with the predicted national crop yield is lower because to achieve the same probability of covering the true national yield a range of 80 bushels per acre is needed instead of 15 bushels per acre. The advantage to receiving an associated prediction interval is that it allows the user to better understand the certainty behind the predicted national crop yield value.

In an embodiment, a distribution set associated with the predicted national crop yield value may be calculated to provide further information of the predicted national crop yield. For instance, by providing the entire distribution set, a user may further calculate risk, revenue, or other predictions based upon the distribution set of yield values.

Remote Sensing

Remote sensors measure spectral bands related to visible and near-infrared light reflected by the land surface. Detecting the level of vegetation in a particular geographic region may be performed using computing elements programmed to execute a mathematical combination and/or transformation between different remotely sensed spectral ranges that accentuate the spectral properties in plants. These combinations are referred to as Vegetation Indices.

In an embodiment, the aggregated time series module 112 may be configured to select different Vegetation Indices in order to evaluate different spectral properties. One such Vegetation Index available is the normalized difference vegetation index (NDVI). NDVI may be used to analyze remotely sensed signals and determine whether a particular area contains live green vegetation. Live green plants absorb solar radiation within the range of 400-700 nanometers (nm), such as visible red (620-670 nm), and scatter solar radiation from the near-infrared (NIR) spectral region (841-876 nm). Meaning that mature green plants with many leaves would absorb visible red for photosynthesis purposes and simultaneously reflect back NIR radiation. The NDVI is calculated as a near-infrared/red ratio between the NIR and the visible red region.

NDVI=(NIR−red)/(NIR+red)

A high NDVI value means that the land region sensed contain a high density of green vegetation.

In an embodiment, the aggregated time series module 112 may be configured to select the green normalized difference vegetation index (GNDVI). The GNDVI, like NDVI measures the amount of green vegetation over a particular area. GNDVI measures solar radiation over a visible green wavelength range (545-565 nm). The GNDVI is calculated as a near-infrared/green ratio between the NIR and the visible green region.

NDVI=(NIR−green)/(NIR+green)

In an embodiment, the aggregated time series module 112 may be configured to select the normalized difference water index (NDWI). The NDWI may also be used to analyze remotely sensed signals and determine the amount of water within vegetation. The benefit to selecting NDWI data is that it is less sensitive to atmospheric effects than NDVI. Atmospheric effects due to atmospheric gases and aerosol particles may distort remotely sensed data by scattering or absorbing direct or reflected sunlight. The NDWI is calculated as a ratio between different near-infrared spectral regions:

NDWI=(NIR−NIR$_2$)/(NIR+NIR$_2$)

Where NIR$_2$ covers wavelengths between 1230-1250 nm.

In an embodiment, the aggregated time series module 112 may be configured to select variant of the NDWI index called fNDWI. Like the NDWI, the fNDWI may be used to analyze remotely sensed signals and determine the amount of water within vegetation. The fNDWI is calculated as a ratio between the near-infrared spectral region (NIR) and an infrared region covering wavelengths between 1628-1652 nm (shortIR):

NDWI=(NIR−short$IR$)/(NIR+short$IR$)

The benefit of using fNDWI over NDWI is that NIR$_2$ values may be noisy or suffer from saturation. By using shortIR the saturation can be mitigated.

In an embodiment, the aggregated time series module 112 may be configured to select the enhanced vegetation index (EVI). The EVI is optimized to enhance the vegetation signal with improved sensitivity in high biomass regions by decoupling a canopy background signal and reducing atmospheric influences. The EVI is calculated as follows:

$$EVI = G \times \frac{(NIR - \text{red})}{(NIR + C_1 \times \text{red} - C_2 \times \text{blue} + L)}$$

Where:

G is a specific gain factor, coefficients $C_1$ and $C_2$ are related to the aerosol resistance term, L is a canopy background adjustment factor, and blue refers to the visible blue wavelength (459-479 nm).

Using multiple vegetation indexes the agricultural intelligence computer system 110 is able to quantify the level of live crops, such as corn, planted in particular areas.

Soil Moisture Data

The North America LDAS provide soil moisture data sets for several land surface data models. The land surface models provide a $\frac{1}{8}^{th}$ degree topographical grid resolution of regions of North America. The soil moisture data sets for specific geo-locations at specific times may be aggregated into geo-specific time series which then may be further aggregated into an aggregated time series for a geographic area. In an embodiment, feature selection may be determined by computing average soil moisture over a particular range. For example, the average soil moisture may be calculated for every 5-day window over the entire season. Then the average soil moistures may be compared to an historical climatology average in order to discover soil moisture anomalies. For example, a historical climatology average for a specific region may be calculated over a 30 year period. Then soil moisture anomalies may be determined by comparing the calculated 5-day average soil moisture for a given region to the historical climatology average for that specific region. The soil moisture anomalies may then be extracted as selected features, such as relative wetness or relative dryness, for a covariate matrix.

Aggregated Time Series

The aggregated time series module 112 may be configured to preprocess the geo-specific time series before creating one or more aggregated time series that each represents a specific geographic area, thus producing more accurate aggregated time series.

In an embodiment, the set of geo-specific time series corresponding to a specific geographic area may be smoothed by programming the aggregated time series module 112 to implement a locally weighted scatterplot smoothing technique. Locally weighted scatterplot smoothing is a method of using locally weighted linear regression to smooth data. The process is local because each smoothed value is determined by neighboring data points defined within the span. The process is weighted because a regression weight function is defined for the data points within the span.

Figure 4:
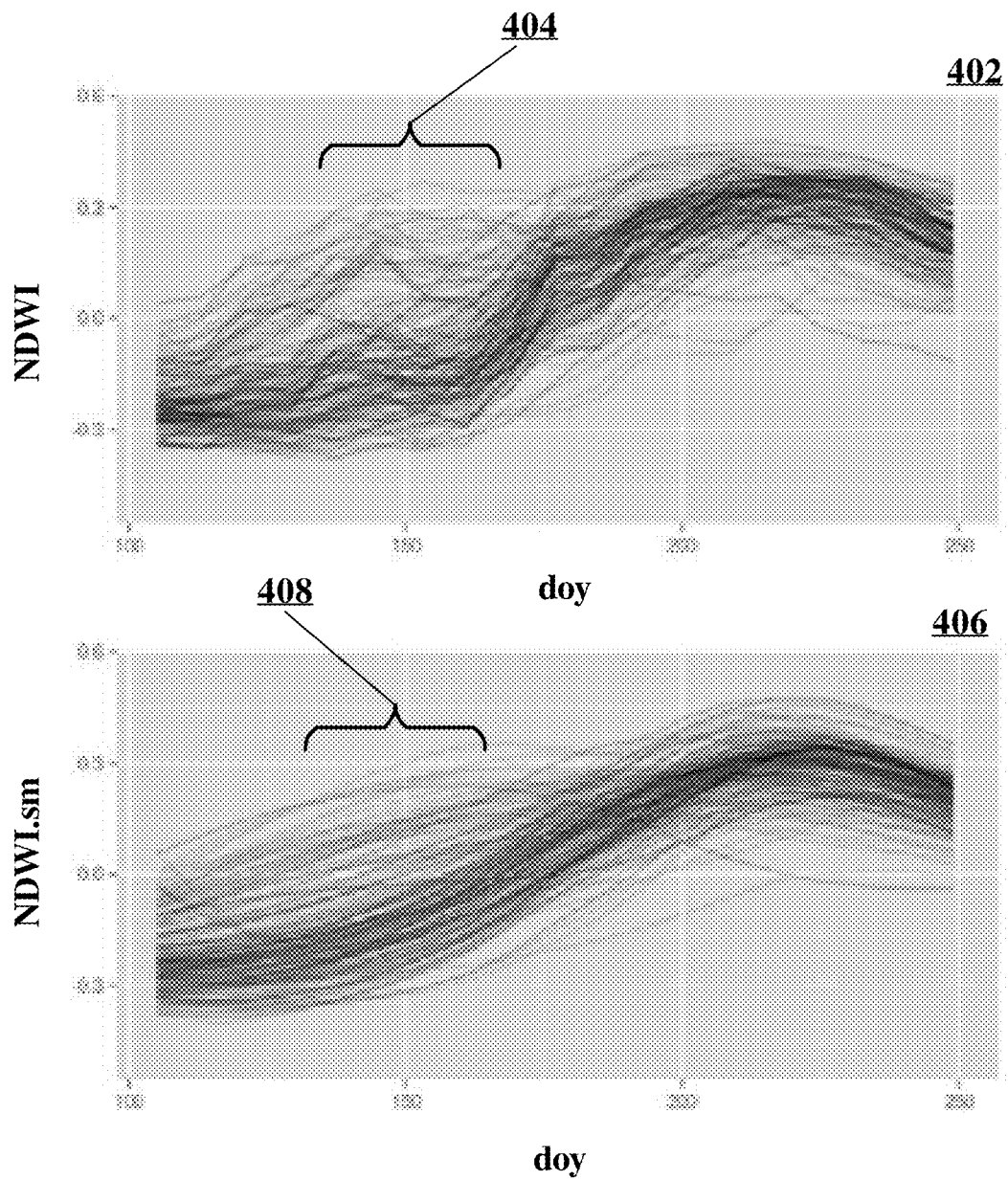
FIG. 4 illustrates an application of locally weighted scatterplot smoothing to a plurality of aggregated time series.

FIG. 4 illustrates applying the locally weighted scatterplot smoothing to NDWI remotely sensed signals in a set of geo-specific time series representing Iowa. Graph 402 depicts the set of geo-specific time series of Iowa before applying locally weighted scatterplot smoothing. As shown by region 404, there are many erratic outliers where the peaks are spread from about day-of-year (doy) 125 to doy 170.

Graph 406 depicts the set of geo-specific time series of Iowa after applying locally weighted scatterplot smoothing. As shown by region 408 the same erratic peaks have been smoothed out and create a generalized trend between each of the time series. By applying locally weighted scatterplot smoothing to the set of geo-specific time series the median value used to create a single time series for the geographic area more accurately depicts the overall crop conditions for that specific year.

Time Series Features

Feature selection of the aggregated time series to properly forecast a yearly output may include using different mathematical functions of the aggregated time series in the programming of the functional units of the system. In an embodiment, the integral of aggregated time series values over a certain time period may be used as a representative feature. For example, the integral of aggregated time series values between day of year 175 and 225 may be determined as a representative feature. Other embodiments may use a shorter time period such as 8 or 10 days for the integral range.

In an embodiment, the integral over a certain period of time divided by the mean of the aggregated time series values above a minimum threshold may be used as a representative feature.

In another embodiment, the value before or after the maximum value may be used as a representative feature of the aggregated time series. Using a value either before or after the maximum value would be useful if the maximum value suffered from an oversaturation and would therefore unnecessarily skew crop yield predictions.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 5:
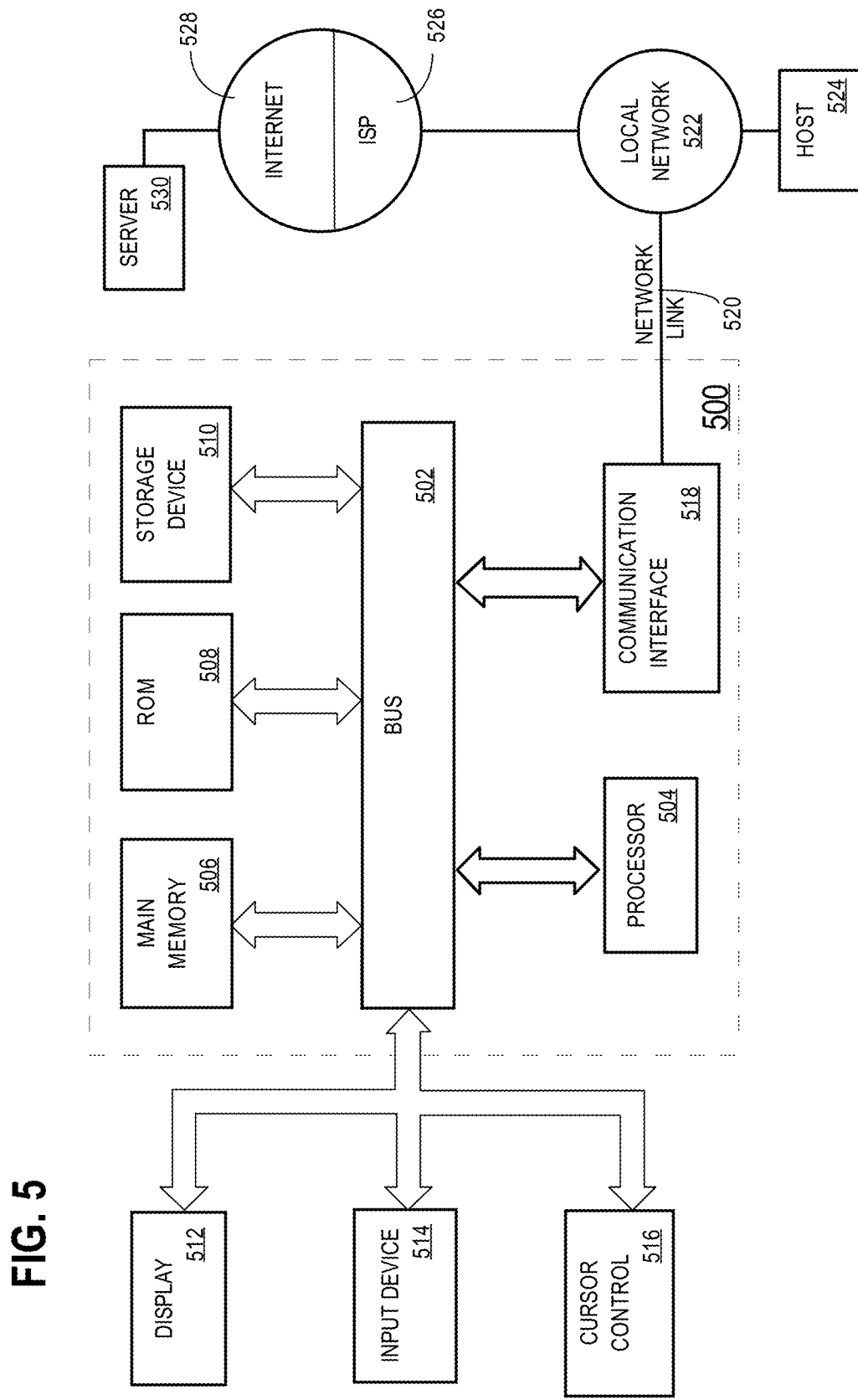
FIG. 5 illustrates a computer system upon which an embodiment may be implemented.

For example, FIG. 5 is a block diagram that illustrates a computer system 500 upon which an embodiment of the invention may be implemented. Computer system 500 includes a bus 502 or other communication mechanism for communicating information, and a hardware processor 504 coupled with bus 502 for processing information. Hardware processor 504 may be, for example, a general purpose microprocessor.

Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Such instructions, when stored in non-transitory storage media accessible to processor 504, render computer system 500 into a special-purpose machine that is customized to perform the operations specified in the instructions.

Computer system 500 further includes a read only memory (ROM) 508 or other static storage device coupled to bus 502 for storing static information and instructions for processor 504. A storage device 510, such as a magnetic disk, optical disk, or solid-state drive is provided and coupled to bus 502 for storing information and instructions.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 may implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor 504 executing one or more sequences of one or more instructions contained in main memory 506. Such instructions may be read into main memory 506 from another storage medium, such as storage device 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 510. Volatile media includes dynamic memory, such as main memory 506. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 502. Transmission media can also take the form of acoustic or light waves, such as those generated during radio-wave and infra-red data communications.

Various forms of media may be involved in carrying one or more sequences of one or more instructions to processor 504 for execution. For example, the instructions may initially be carried on a magnetic disk or solid-state drive of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a local network 522. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN. Wireless links may also be implemented. In any such implementation, communication interface 518 sends and receives electrical, electromagnetic or optical signals that carry digital data streams representing various types of information.

Network link 520 typically provides data communication through one or more networks to other data devices. For example, network link 520 may provide a connection through local network 522 to a host computer 524 or to data equipment operated by an Internet Service Provider (ISP) 526. ISP 526 in turn provides data communication services through the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are example forms of transmission media.

Computer system 500 can send messages and receive data, including program code, through the network(s), network link 520 and communication interface 518. In the Internet example, a server 530 might transmit a requested code for an application program through Internet 528, ISP 526, local network 522 and communication interface 518.

The received code may be executed by processor 504 as it is received, and/or stored in storage device 510, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A method comprising:
  using digitally programmed instructions in an agricultural intelligence computer system, receiving one or more agricultural data records that represent a type of covariate data value for plants at a specific geo-location at a specific time, wherein the type of covariate data value includes at least one of a remotely sensed spectral property of plant records at a particular spectral bandwidth range, and a soil moisture record;
  using the digitally programmed instructions in the agricultural intelligence computer system, aggregating the one or more agricultural data records to create one or more geo-specific time series, wherein each geo-specific time series represents a specific geo-location over a specified time;
  using the digitally programmed instructions in the agricultural intelligence computer system, creating one or more aggregated time series for each of one or more specific geographic areas, for each geographic area of the one or more specific geographic areas:
  applying locally weighted scatterplot smoothing to a subset of the one or more geo-specific time series for the respective geographic area;
  selecting median values from each time interval to create an aggregated time series for the respective geographic area;
  using the digitally programmed instructions in the agricultural intelligence computer system, selecting a representative feature from the one or more aggregated time series and creating for each specific geographic area a covariate matrix in computer memory comprising the representative features selected from the one or more aggregate time series;
  using the digitally programmed instructions in the agricultural intelligence computer system, determining a specific state crop yield for a specific state and a specific year by using linear regression to calculate the specific state crop yield from the covariate matrix that represents the specific state for that specific year, wherein one or more regression coefficients for the specific state are calculated by using a normal distribution function and wherein an error term for the specific state is calculated by using the normal distribution function where a mean parameter is zero and a variance parameter is a state specific bias coefficient;
  calculating a mean parameter for the normal distribution function wherein the mean parameter comprises a sum of each specific state crop yield multiplied by a specific state weighted value, multiplied by a first national bias coefficient, and added to a second national bias coefficient, wherein the specific state weighted value is determined as a relative weighted value based upon specific state crop yields of other states;
  calculating a variance parameter for the normal distribution function wherein the variance parameter comprises a sum of each specific state bias coefficient squared multiplied by the specific state weighted value, multiplied by the first national bias coefficient squared, and added to a third national bias coefficient squared;
  using the digitally programmed instructions in the agricultural intelligence computer system, determining a national crop yield for the specific year by using the mean parameter and the variance parameter from the normal distribution function to calculate the national crop yield for the specific year from a sum of multiple specific state crop yields for the specific year nationally adjusted using bias coefficients that account for biases and errors caused by incomplete sampling of the multiple specific state crop yields;
  determining a prediction interval associated with the national crop yield, wherein the prediction interval is range of values that measures a level of certainty associated with the national crop yields;
  receiving a request for the national crop yield for the specific year from a client computer;
  determining a mean projected revenue for a particular farm based on the national crop yield for the specific year;
  determining a recommendation for the particular farm based on the mean projected revenue for the particular farm;

in response to receiving the request causing display, on a graphical user interface at the client computer, of the national crop yield for the specific year; and providing, to a client machine associated with the particular farm, the recommendation for the particular farm.

2. The method of claim 1, wherein aggregating the one or more agricultural data records to create one or more geo-specific time series further comprises filtering one or more agricultural data records that correspond to known geo-locations that are not used as agricultural growth areas.

3. The method of claim 1, wherein aggregating the one or more agricultural data records to create one or more geo-specific time series further comprises selecting favorable data values from the one or more agricultural data records based upon a vegetation index, wherein a vegetation index is a combination of one or more wavelength ranges of remotely sensed spectral properties.

4. The method of claim 1, wherein aggregating the one or more agricultural data records to create one or more geo-specific time series comprises aggregating soil moisture data records that correspond to a specific geo-location at a specific point in time.

5. The method of claim 1, wherein selecting a representative feature from the one or more aggregated time series comprises selecting one of the following: a maximum value of the aggregated time series, an integral over a specified time period of the aggregated time series, an integral over a specified time period of the aggregated time series divided by a mean of the aggregated time series provided the mean is above a defined value threshold, an aggregated time series value at a period of time before the maximum value of the aggregated time series, or an aggregated time series value at a period of time after the maximum value of the aggregated time series.

6. The method of claim 1, wherein the aggregated time series represents a specific state in a country.

7. The method of claim 1, wherein determining the specific state crop yield for the specific year by applying the normal distribution function comprises using independent and identically distributed random variables.

8. The method of claim 1, wherein determining the national crop yield for the specific year by applying the normal distribution function comprises using independent and identically distributed random variables.

9. The method of claim 1, wherein determining a national crop yield for the specific year further comprises determining a distribution set associated with the national crop yield, wherein the distribution set measures a level of certainty associated with the national crop yield.

10. One or more non-transitory storage media storing instructions which, when executed by one or more computing devices, cause performance of a method comprising the steps of:

using digitally programmed instructions in an agricultural intelligence computer system, receiving one or more agricultural data records that represent a type of covariate data value for plants at a specific geo-location at a specific time, wherein the type of covariate data value includes at least one of a remotely sensed spectral property of plant records at a particular spectral bandwidth range, and a soil moisture record;

using the digitally programmed instructions in the agricultural intelligence computer system, aggregating the one or more agricultural data records to create one or more geo-specific time series, wherein each geo-specific time series represents a specific geo-location over a specified time;

using the digitally programmed instructions in the agricultural intelligence computer system, creating one or more aggregated time series for each of one or more specific geographic areas, for each geographic area of the one or more specific geographic areas:

applying locally weighted scatterplot smoothing to a subset of the one or more geo-specific time series for the respective geographic area;

selecting median values from each time interval to create an aggregated time series for the respective geographic area;

using the digitally programmed instructions in the agricultural intelligence server computer system, selecting a representative feature from the one or more aggregated time series and creating for each specific geographic area a covariate matrix in computer memory comprising the representative features selected from the one or more aggregate time series;

using digitally programmed instructions in the agricultural intelligence computer system, determining a specific state crop yield for a specific state and a specific year by using linear regression to calculate the specific state crop yield from the covariate matrix that represents the specific state for that specific year, wherein one or more regression coefficients for the specific state are calculated by using a normal distribution function and wherein an error term for the specific state is calculated by using the normal distribution function where a mean parameter is zero and a variance parameter is a state specific bias coefficient;

calculating a mean parameter for the normal distribution function wherein the mean parameter comprises a sum of each specific state crop yield multiplied by a specific state weighted value, multiplied by a first national bias coefficient, and added to a second national bias coefficient, wherein the specific state weighted value is determined as a relative weighted value based upon specific state crop yields of other states;

calculating a variance parameter for the normal distribution function wherein the variance parameter comprises a sum of each specific state bias coefficient squared multiplied by the specific state weighted value, multiplied by the first national bias coefficient squared, and added to a third national bias coefficient squared;

using the digitally programmed instructions in the agricultural intelligence computer system, determining a national crop yield for the specific year by using the mean parameter and the variance parameter from the normal distribution function to calculate the national crop yield for the specific year from a sum of multiple specific state crop yields for the specific year nationally adjusted using bias coefficients that account for biases and errors caused by incomplete sampling of the multiple specific state crop yields;

determining a prediction interval associated with the national crop yield, wherein the prediction interval is range of values that measures a level of certainty associated with the national crop yields;

receiving a request for the national crop yield for the specific year from a client computer;

determining a mean projected revenue for a particular farm based on the national crop yield for the specific year;

determining a recommendation for the particular farm based on the mean projected revenue for the particular farm;

in response to receiving the request causing display, on a graphical user interface at the client computer, of the national crop yield for the specific year; and providing, to a client machine associated with the particular farm, the recommendation for the particular farm.

11. The one or more non-transitory storage media of claim 10, wherein aggregating the one or more agricultural data records to create one or more geo-specific time series further comprises filtering one or more agricultural data records that correspond to known geo-locations that are not used as agricultural growth areas.

12. The one or more non-transitory storage media of claim 10, wherein aggregating the one or more agricultural data records to create one or more geo-specific time series further comprises selecting favorable data values from the one or more agricultural data records based upon a vegetation index, wherein a vegetation index is a combination of one or more wavelength ranges of remotely sensed spectral properties.

13. The one or more non-transitory storage media of claim 10, wherein aggregating the one or more agricultural data records to create one or more geo-specific time series comprises aggregating soil moisture data records that correspond to a specific geo-location at a specific point in time.

14. The one or more non-transitory storage media of claim 10, wherein selecting a representative feature from the one or more aggregated time series comprises selecting one of the following: a maximum value of the aggregated time series, an integral over a specified time period of the aggregated time series, an integral over a specified time period of the aggregated time series divided by a mean of the aggregated time series provided the mean is above a defined value threshold, an aggregated time series value at a period of time before the maximum value of the aggregated time series, or an aggregated time series value at a period of time after the maximum value of the aggregated time series.

15. The one or more non-transitory storage media of claim 10, wherein the aggregated time series represents a specific state in a country.

16. The one or more non-transitory storage media of claim 10, wherein determining the specific state crop yield for the specific year by applying the normal distribution function comprises using independent and identically distributed random variables.

17. The one or more non-transitory storage media of claim 10, wherein determining the national crop yield for the specific year by applying the normal distribution function comprises using independent and identically distributed random variables.

18. The one or more non-transitory storage media of claim 10, wherein determining a national crop yield for the specific year further comprises determining a distribution set associated with the national crop yield, wherein the distribution set measures a level of certainty associated with the national crop yield.

* * * * *

UNITED STATES PATENT AND TRADEMARK OFFICE
CERTIFICATE OF CORRECTION

PATENT NO.        : 10,564,316 B2
APPLICATION NO.   : 14/675992
DATED             : February 18, 2020
INVENTOR(S)       : Ying Xu and Lijuan Xu It is certified that error appears in the above-identified patent and that said Letters Patent is hereby corrected as shown below:

In the Claims

Column 16
Claim 1: Line 59: Delete "yields" and insert --yield--.

Column 18
Claim 10: Line 16: Delete "server"
Line 22: After "using" and before "digitally", insert --the--.
Line 57: Delete "yields" and insert --yield--.

Signed and Sealed this
Seventeenth Day of March, 2020

Andrei Iancu
*Director of the United States Patent and Trademark Office*